United States Patent
Nunes et al.

(10) Patent No.: US 8,025,856 B2
(45) Date of Patent: Sep. 27, 2011

(54) COLORIMETRIC CHEMICAL ANALYSIS SAMPLER FOR THE PRESENCE OF EXPLOSIVES

(75) Inventors: Peter J. Nunes, Danville, CA (US); Joel Del Eckels, Livermore, CA (US); John G. Reynolds, San Ramon, CA (US); Philip F. Pagoria, Livermore, CA (US); Randall L. Simpson, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1365 days.

(21) Appl. No.: 11/208,482

(22) Filed: Aug. 18, 2005

(65) Prior Publication Data
US 2007/0202009 A1 Aug. 30, 2007

Related U.S. Application Data

(60) Provisional application No. 60/629,057, filed on Nov. 17, 2004.

(51) Int. Cl.
*B01L 3/00* (2006.01)
*G01N 21/77* (2006.01)
(52) U.S. Cl. ........................ 422/556; 436/169
(58) Field of Classification Search .................. 422/556; 436/169
See application file for complete search history.

(56) References Cited

U.S. PATENT DOCUMENTS

| | | | | |
|---|---|---|---|---|
| 3,446,596 | A * | 5/1969 | Salivar et al. | 436/110 |
| 4,003,706 | A * | 1/1977 | Szekely | 436/110 |
| 4,635,488 | A * | 1/1987 | Kremer | 73/864.72 |
| 4,788,039 | A * | 11/1988 | Glattstein | 422/61 |
| 5,078,968 | A | 1/1992 | Nason | |
| 5,246,669 | A * | 9/1993 | Hayashi | 422/556 |
| 5,296,380 | A | 3/1994 | Margalit | |
| 5,354,692 | A * | 10/1994 | Yang et al. | 436/514 |
| 5,364,792 | A | 11/1994 | Stone | |
| 5,550,061 | A * | 8/1996 | Stone | 436/73 |
| 5,633,140 | A | 5/1997 | Wex et al. | |
| 5,709,838 | A * | 1/1998 | Porter et al. | 422/61 |
| 6,153,147 | A * | 11/2000 | Craig | 422/59 |
| 6,214,291 | B1 * | 4/2001 | Kerman | 422/61 |
| 6,228,280 | B1 * | 5/2001 | Li et al. | 216/84 |
| 6,863,866 | B2 * | 3/2005 | Kelly et al. | 422/56 |

(Continued)

FOREIGN PATENT DOCUMENTS
EP 058125 A 3/1994

OTHER PUBLICATIONS

Arbuthnot, D., et al., "Detection of a polynitroaromatic compound using a novel polymer-based multiplate sensor," SPIE, vol. 3392, pp. 432-440, date of above of NPL is Apr. 1998.

*Primary Examiner* — Lore Jarrett
(74) *Attorney, Agent, or Firm* — Eddie E. Scott; James S. Tak

(57) ABSTRACT

A tester for testing for explosives comprising a body, a lateral flow swab unit operably connected to the body, a explosives detecting reagent contained in the body, and a dispenser operatively connected to the body and the lateral flow swab unit. The dispenser selectively allows the explosives detecting reagent to be delivered to the lateral flow swab unit.

23 Claims, 3 Drawing Sheets

U.S. PATENT DOCUMENTS

| | | | |
|---|---|---|---|
| 7,285,246 B1* | 10/2007 | Martin | 422/86 |
| 7,410,612 B1* | 8/2008 | Carrington | 422/61 |
| 7,829,020 B2* | 11/2010 | Pagoria et al. | 422/402 |
| 2003/0104506 A1* | 6/2003 | Durst et al. | 435/7.92 |
| 2004/0265169 A1* | 12/2004 | Haas et al. | 422/56 |
| 2005/0101027 A1* | 5/2005 | Haas | 436/109 |
| 2006/0172438 A1* | 8/2006 | Milunic et al. | 436/524 |
| 2008/0069728 A1* | 3/2008 | Attar et al. | 422/58 |

* cited by examiner

COLORIMETRIC CHEMICAL ANALYSIS SAMPLER FOR THE PRESENCE OF EXPLOSIVES

CROSS-REFERENCE TO RELATED APPLICATIONS

This application claims the benefit of U.S. Provisional Patent Application No. 60/629,057 filed Nov. 17, 2004 by Peter J. Nunes, Joel Del Eckels, John G. Reynolds, Philip F. Pagoria, and Randall L. Simpson, titled "Colorimetric Chemical Analysis Sampler for the Presence of Explosives." U.S. Provisional Patent Application No. 60/629,057 filed Nov. 17, 2004 titled "Colorimetric Chemical Analysis Sampler for the Presence of Explosives" is incorporated herein by this reference. The following applications contain related subject matter and are owned by the common assignee, Lawrence Livermore National Security, LLC for the operation of Lawrence Livermore National Laboratory: U.S. patent application Ser. No. 11/165,474, Filed Jun. 22, 2005, for Chemical Analysis Coupon for the Presence of Explosives; U.S. patent application Ser. No. 11/158,480, Filed Jun. 21, 2005 for Chemical Analysis Kit for the Presence of Explosives; U.S. patent application Ser. No. 11/159,451, Filed Jun. 22, 2005 for Spot Test Kit for Explosives Detection; U.S. patent application Ser. No. 11/525,655, Filed Sep. 21, 2006 for Explosives Tester with Heater; U.S. patent application Ser. No. 11/593,257, Filed Nov. 1, 2006 for Explosives Tester with Heater; and U.S. patent application Ser. No. 11/634,784, Filed Dec. 5, 2006 for Low to Moderate Temperature Nanolaminate Heater; which are incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to explosives and more particularly to testing for the presence of explosives.

2. State of Technology

U.S. Pat. No. 5,638,166 for an apparatus and method for rapid detection of explosives residue from the deflagration signature thereof issued Jun. 10, 1997 to Herbert O. Funsten and David J. McComas and assigned to The Regents of the University of California provides the following state of the art information, "Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. See, Fetterolf et al., Portable Instrumentation: New Weapons in the War Against Drugs and Terrorism," Proc. SPIE 2092 (1993) 40, Yinon and Zitrin, in Modern Methods and Applications in Analysis of Explosions, (Wiley, New York, 1993) Chap. 6; and references therein. Vapor detection is achieved using trained animals, gas chromatography, ion mobility mass spectrometry, and bioluminescence, as examples. All of these techniques suffer from the inherently low vapor pressures of most explosives. Bulk detection of explosives may be performed using x-ray imaging which cannot detect the explosives themselves, but rather detects metallic device components. Another method for bulk detection involves using energetic x-rays to activate nitrogen atoms in the explosives, thereby generating positrons which are detected. This technique requires an x-ray generator and a minimum of several hundred grams of explosives. Bulk detection is also accomplished using thermal neutron activation which requires a source of neutrons and a .gamma.-radiation detector. Thus, bulk detection is not sensitive to trace quantities of explosives and requires large, expensive instrumentation. Tagging requires that all explosives be tagged with, for example, an easily detected vapor. However, since tagging is not mandatory in the United States, this procedure is clearly not reliable. It turns out that there are no technologies for performing accurate, real-time (<6 sec) detection and analysis of trace explosives in situ. Only trained dogs can achieve this goal.

It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," J. Forensic Science 27 (1982) 783; J. D. Twibell et al., "The Persistence of Military Explosives on Hands," J. Forensic Science 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives.

U.S. Pat. No. 5,679,584 for a method for chemical detection issued Oct. 2, 1997 to Daryl Sunny Mileaf and Noe Esau Rodriquez, II provides the following state of the art information, "a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction."

U.S. Pat. No. 6,470,730 for a dry transfer method for the preparation of explosives test samples issued Oct. 29, 2002 to Robert T. Chamberlain and assigned to The United States of America as represented by the Secretary of Transportation provides the following state of the art information, "method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a tester for testing for explosives. The tester comprises a body, a lateral flow swab unit operably connected to the body, an explosives detecting reagent contained in the body, and a dispenser operatively connected to the body and the lateral flow swab unit. The dispenser selectively allows the explosives detecting reagent to be delivered to the lateral flow swab unit. In one embodiment the lateral flow swab unit comprises a microporous membrane swab. Operation of the tester starts by the dispenser allowing the explosives detecting reagent to be delivered to the lateral flow swab unit. The swab unit is swiped across the surface of to be tested. Any suspect substance will be picked up by the swab surface. If the swab surface becomes colored, the test is positive for explosives.

The tester of the present invention provides a simple, chemical, field test to provide a rapid screen for the presence of a broad range of explosive residues. The tester is fast, low-cost, very easy to use, and provides a very low rate of false positives. The tester provides a fast, sensitive, low-cost, very easy to implement system for testing the suspected packages. The tester is inexpensive and disposable. A large number of common military and industrial explosives can be easily detected such as HMX, RDX, NG, TATB, Tetryl, PETN, TNT, DNT, TNB, DNB and NC. The tester is small enough that a number of them can fit in a pocket or brief case.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
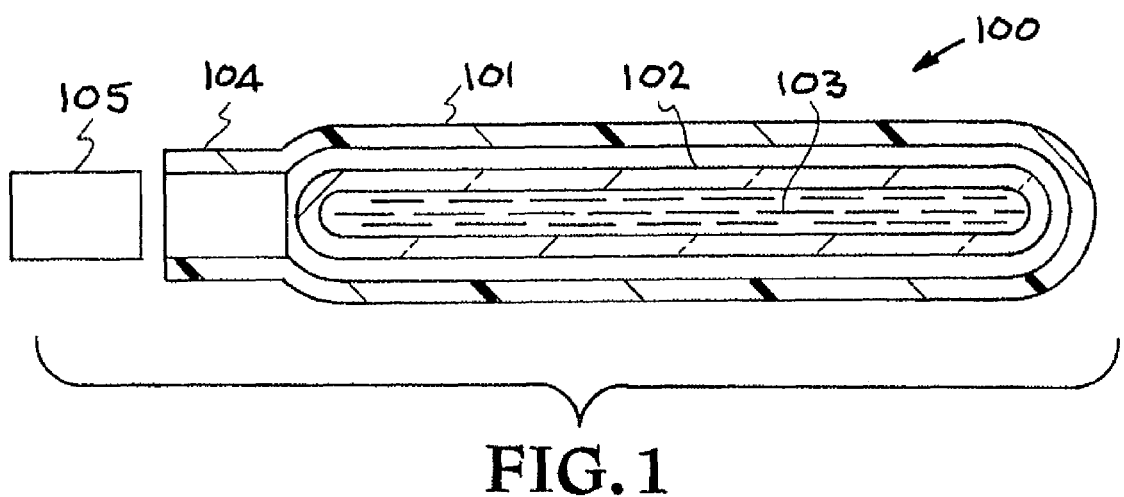
FIG. 1 illustrates an embodiment of the tester of the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The ability to identify unknown explosives in the field is of utmost importance to the military, law enforcement and Homeland security forces worldwide. There have been many reports of the use of spot tests for the identification of explosives, some of which are listed below. They have been used in combination with thin-layer chromatography and in forensic analysis. There are some commercial companies (Mistral, Securesearch, Duram products) who have produced explosives identification kits similar to the one Applicants propose. They have incorporated similar color reagents and have been used by the military and law-enforcement agencies. Ex-spray and Duram products are probably the best commercial test kits produced thus far. They allow the identification of nitroaromatics, nitramines, ammonium nitrate, and recently the potassium chlorate-based explosives. Their systems are available as spray kits or solution-drop kits. The Duram product will also identify the peroxide explosives. Another company produced a swab kit that incorporates either diphenylamine or Wurster's salt that turns blue when it comes in contact with nitramines, oxidizers and nitrate esters. It is easy to use but is non-specific and would give a significant number of false positives.

Figure 2:
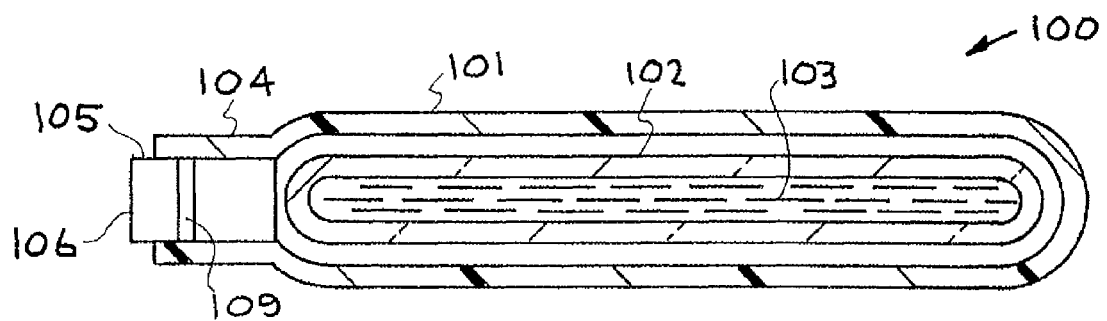
FIG. 2 is another view of the tester.

Referring to the drawings, and in particular to FIG. 1 and FIG. 2, an embodiment of a tester constructed in accordance with the present invention is illustrated. This embodiment of the present invention is designated generally by the reference numeral 100. FIG. 1 shows the tester 100 in an exploded view and FIG. 2 shows the tester 100 in an assembled configuration. The tester 100 is an inexpensive and disposable device. The tester 100 can be used anywhere as a primary screening tool by non-technical personnel to determine whether a surface contains explosives. The tester 100 was developed to allow identification of explosives. This tester may be of used by first responders, military, law enforcement and Homeland Security.

The tester 100 provides a small, disposable, one use system. The tester 100 uses a simple and rapid method of operation. The structure of the tester 100 includes a body 101. The body 101 is made of a squeezable material such as plastic. An ampoule 102 containing an explosives detecting reagent 103 is located within the squeezable body 101. An outlet 104 in the body 101 allows the explosives detecting reagent 103 to be dispensed for detecting explosives as will be subsequently described. A lateral flow swab unit 105 is operably positioned in the outlet 104. The ampoule 102 containing the explosives detecting reagent 103 is a breakable ampoule and acts as a dispenser for selectively allowing the explosives detecting reagent 103 to be delivered to the lateral flow swab unit 105.

The lateral flow swab unit 105 comprises a microporous membrane material that provides migration of the explosives detecting reagent 103 from the ampoule 102 and the body 101. Lateral flow membrane materials are known for their use in other fields. Lateral flow membrane material is known for use as blotting techniques, enzyme-linked immunosorbent assay (ELISA) testing, and lateral-flow immunochromatographic tests. The lateral flow swab unit 105 comprises polyethylene spheres fused into a lateral flow membrane. The lateral flow swab unit 105 is a Porex Lateral-Flo Membrane. Applicants experimentally determined that the properties of the lateral flow swab unit 105 make it an ideal swipe material for the tester 100. The lateral flow membrane 105 is chemical resistant, withstands heat as high as 130° C., is durable, is inexpensive, can be formed in any size, and concentrates suspect materials along the solvent front 109 making colorimetric detection limits. The lateral flow swab unit 105 includes a surface area 106 swipe for sample collection.

Figure 3:
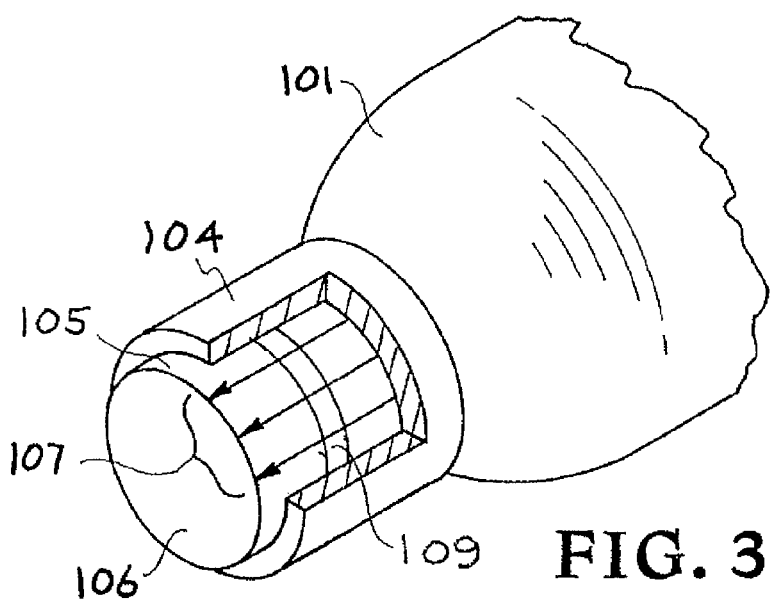
FIG. 3 shows details of the tester.

Referring now to FIG. 3, details of the lateral flow swab unit 105 are illustrated. The lateral flow swab unit 105 is made a microporous membrane material that provides migration of the explosives detecting reagent from the ampoule and the body. This is illustrated by the arrows 107 which show the explosives detecting reagent wicking along the outside surface of the lateral flow swab unit 105. The explosives detecting reagent wicks along the outside surface of the lateral flow swab unit 105 to the surface 106 of the lateral flow swab unit 105. The surface area 106 provides a swipe area for sample collection. The lateral flow swab unit 105 comprises polyethylene spheres fused into a lateral flow membrane. The lateral flow swab unit 105 is a Porex Lateral-Flo Membrane. Applicants experimentally determined that the properties of the lateral flow swab unit 105 make it an ideal swipe material for the tester 100. The lateral flow membrane 105 is chemical resistant, withstands heat as high as 130° C., is durable, is inexpensive, can be formed in any size, and concentrates suspect materials along the solvent front 109 making colorimetric detection limits.

Figure 4:
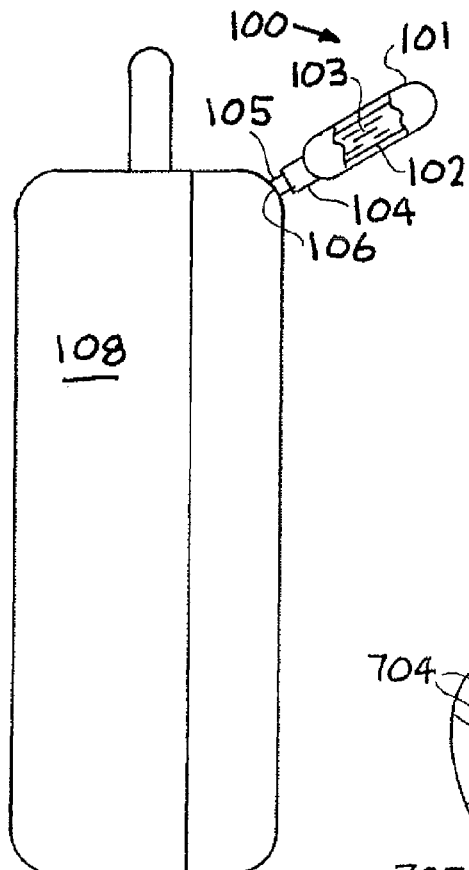
FIG. 4 shows operation of the tester.

Referring to FIG. 4, the operation of the tester 100 is illustrated. The swab surface 106 of the lateral flow swab unit 105 is exposed to the suspect substance. This is accomplished by the swab surface 106 being swiped across a surface containing the suspect substance. As illustrated in FIG. 4, the swab surface 106 is swiped across the surface of a suitcase 108.

The operation of the tester 100 starts by breaking the ampoule 102 containing the explosives detecting reagent 103 located within the squeezable body 101. This is accomplished by squeezing the body 101 and breaking the ampoule 102. The ampoule 102 acts as a dispenser allowing the explosives detecting reagent 103 to be delivered to the lateral flow swab unit 105 and the swab surface 106. The swab surface 106 is swiped across the surface of the suitcase 108. Any suspect substance will be picked up by the swab surface 106. If the swab surface 106 becomes colored, the test is positive for explosives.

The tester 100 provides a small, disposable, one use system. The tester 100 uses a simple and rapid method of operation. The tester 100 is an inexpensive and disposable device. The tester 100 can be used anywhere as a primary screening tool by non-technical personnel to determine whether a surface contains explosives. The tester 100 allows identification of explosives. This tester can be used by first responders, military, law enforcement, Homeland Security, and others.

Figure 5:
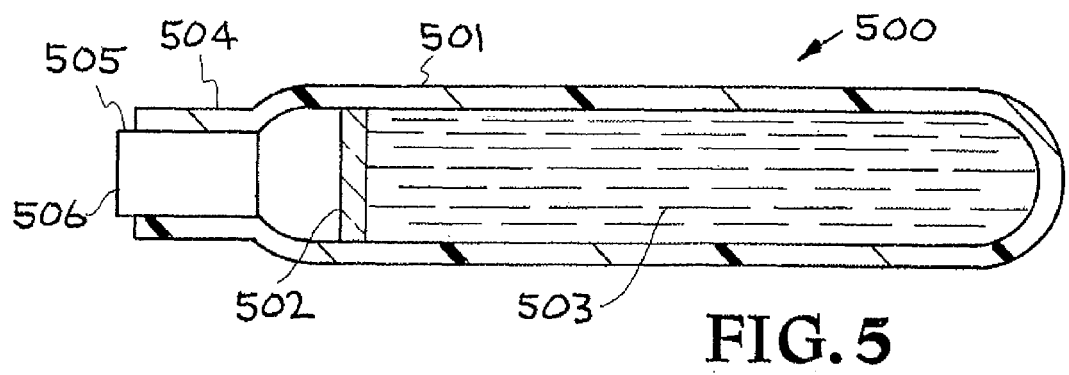
FIG. 5 shows another embodiment of a tester constructed in accordance with the present invention.

Referring now to FIG. 5, another embodiment of a tester constructed in accordance with the present invention is illustrated. This embodiment of the present invention is designated generally by the reference numeral 500. The structure of the tester 500 includes a body 501. The body 501 is made of a squeezable material such as plastic. The explosives detecting reagent 503 is located within the squeezable body 501. A breakable valve 502 seals the body 501 keeping the explosives detecting reagent 503 in place until the testing operation is started. An outlet 504 in the body 501 allows the explosives detecting reagent 503 to be dispensed for detecting explosives as will be subsequently described. A lateral flow swab unit 505 is operably positioned in the outlet 504. The lateral flow swab unit 505 comprises a microporous membrane material that provides migration of the explosives detecting reagent 503 from the ampoule 502 and the body 501. The lateral flow swab unit 505 includes a surface area 506 swipe for sample collection.

The operation of the tester 500 starts by breaking the breakable valve 502 releasing the explosives detecting reagent 503 located within the body 501. This is accomplished by squeezing the body 501 and breaking the breakable valve 502. This allows the explosives detecting reagent 503 to be delivered to the lateral flow swab unit 505 and the swab surface 506. The swab surface 506 is swiped across the surface of the area to be tested. Any suspect substance will be picked up by the swab surface 506. If the swab surface 506 becomes colored, the test is positive for explosives.

The tester 500 provides a small, disposable, one use system. The tester 500 uses a simple and rapid method of operation. The tester 500 is an inexpensive and disposable device. The tester 500 can be used anywhere as a primary screening tool by non-technical personnel to determine whether a surface contains explosives. The tester 500 was developed to allow identification of explosives. This tester may be used by first responders, military, law enforcement and Homeland Security.

Figure 6:
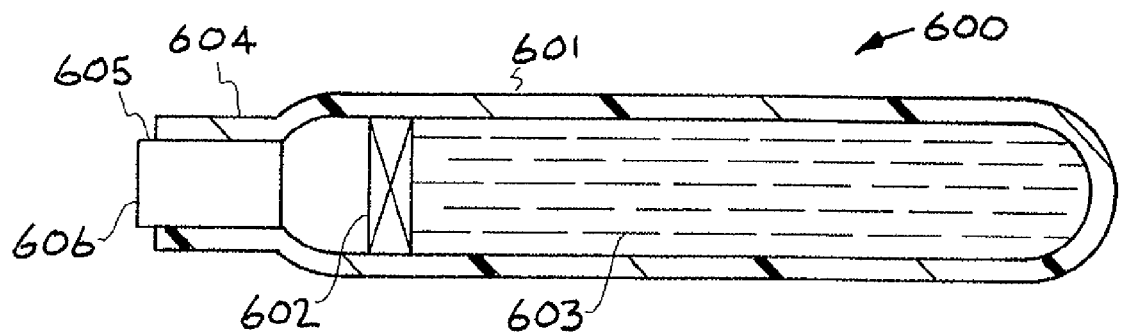
FIG. 6 shows yet another embodiment of a tester constructed in accordance with the present invention.

Referring now to FIG. 6, yet another embodiment of a tester constructed in accordance with the present invention is illustrated. This embodiment of the present invention is designated generally by the reference numeral 600. The structure of the tester 600 includes a body 601. The body 601 is made of a squeezable material such as plastic. The explosives detecting reagent 603 is located within the squeezable body 601. A valve 602 seals the body 601 keeping the explosives detecting reagent 603 in place until the testing operation is started. An outlet 604 in the body 601 allows the explosives detecting reagent 603 to be dispensed for detecting explosives as will be subsequently described. A lateral flow swab unit 605 is operably positioned in the outlet 604. The lateral flow swab unit 605 comprises a microporous membrane material that provides migration of the explosives detecting reagent 603 from the ampoule 602 and the body 601. The lateral flow swab unit 605 includes a surface area 606 swipe for sample collection.

The operation of the tester 600 starts by opening valve 602 releasing the explosives detecting reagent 603 located within the body 601. This is accomplished by squeezing the body 601 and manipulating the valve 602 to open it. Simple valves are well known and may be used for the valve 502. Opening the valve 505 allows the explosives detecting reagent 603 to be delivered to the lateral flow swab unit 605 and the swab surface 606. The swab surface 606 is swiped across the surface of the area to be tested. Any suspect substance will be picked up by the swab surface 606. If the swab surface 606 becomes colored, the test is positive for explosives.

The tester 600 provides a small, disposable, one use system. The tester 600 uses a simple and rapid method of operation. The tester 600 is an inexpensive and disposable device. The tester 600 can be used anywhere as a primary screening tool by non-technical personnel to determine whether a surface contains explosives. The tester 600 was developed to allow identification of explosives. This tester may be of used by first responders, military, law enforcement and Homeland Security.

Figure 7:
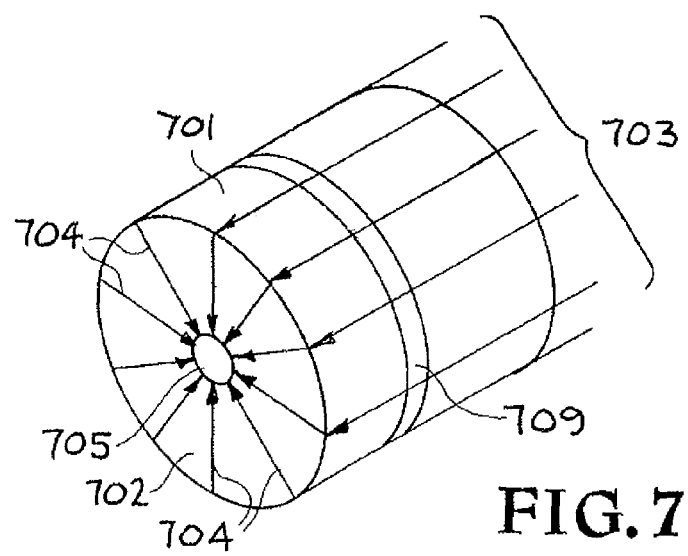
FIG. 7 shows details of the tester.

Referring now to FIG. 7, details of another embodiment of a lateral flow swab unit are illustrated. This embodiment of a lateral flow swab unit is designated by the reference numeral 701. The lateral flow swab unit 701 comprises polyethylene spheres fused into a lateral flow membrane. The lateral flow swab unit 701 is a Porex Lateral-Flo Membrane. Applicants experimentally determined that the properties of the lateral flow swab unit 701 make it an ideal swipe material for the tester. The lateral flow membrane 701 is chemical resistant, withstands heat as high as 130° C., is durable, is inexpensive, can be formed in any size, and concentrates suspect materials along the solvent front 709 making colorimetric detection limits.

The lateral flow swab unit 701 provides migration of the explosives detecting reagent from the body. This is illustrated by the arrows 703 which show the explosives detecting reagent wicking along the outside surface of the lateral flow swab unit 701. The explosives detecting reagent wicks along the outside surface of the lateral flow swab unit 701 to the surface 702 of the lateral flow swab unit 701. The surface area 702 provides a swipe area for sample collection. The explosives detecting reagent is shown wicking onto the surface 702 as illustrated by the arrows 704. The explosives detecting reagent is delivered to the lateral flow swab unit surface 702. The swab surface 702 is swiped across the surface of the area to be tested. Any suspect substance will be picked up by the swab surface 702. Any suspect matter is concentrated as illustrated at 705 which improves the detection capability of the tester. If the swab surface 702 becomes colored, the test is positive for explosives.

Figure 8:
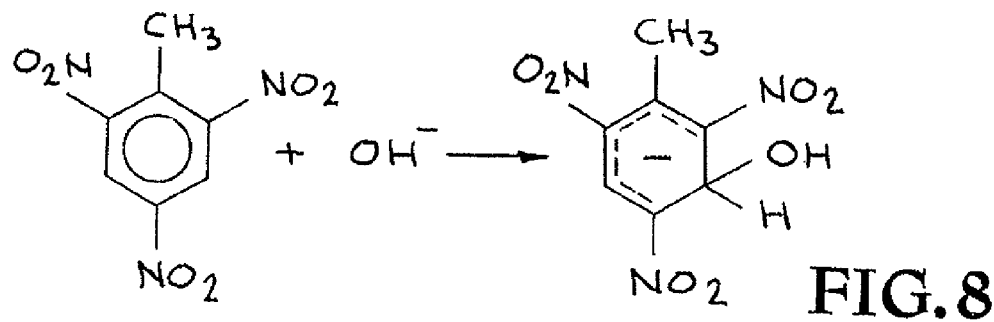
FIG. 8 illustrates the Meisenheimer complex.
Figure 9:
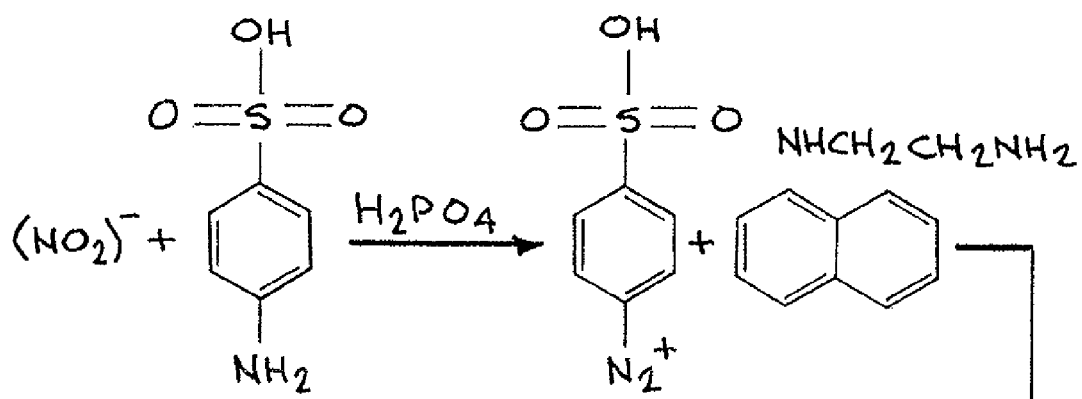
FIG. 9 illustrates the Griess Reagent reaction.
Figure 9:
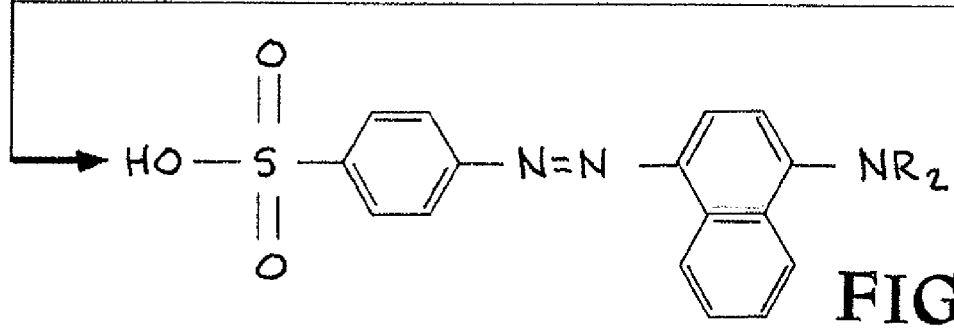

Referring now to FIGS. 8 and 9, two of the colorimetric tests to screen for explosives will be illustrated. The colorimetric chemistry illustrated in FIGS. 8 and 9 incorporates the Meisenheimer complex in FIG. 7 and the Griess Reagent in FIG. 8. The calorimetric chemistry incorporates, but is not limited to, the Meisenheimer complex, the Griess Reagent, Nessler's reagent, and Thymol reaction. The chemistry used in the test for explosives is as follows:

1) Meisenheimer Complex solution is Tetrabutylammonium Hydroxide in Ethanol and gives a color indication for TNT, Tetryl, and Trinitrobenzene.
2) Diphenylamine (DPA) in conc. $H_2SO_4$ gives a color indication for nitramines, nitrate esters, and TATP and other oxidizers (NG, PETN, TATP, RDX, NQ, AN)
3) Nessler's reagent is a solution of mercury (II) iodide, typically around 1.4%, in aqueous potassium and potassium hydroxide iodide and is specific for ammonium cation (AN).
4) Thymol in conc. $H_2SO_4$ gives green color for most nitrate esters. RDX and HMX give a red color.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An explosives tester apparatus for testing a suspect material for explosives wherein the suspect material may contain explosives, comprising:
   a bottle shaped container explosives tester body with a mouth outlet, a lateral flow swab unit positioned in said mouth outlet of said explosives tester body,
   the suspect material located on said lateral flow membrane swab unit when said lateral flow membrane swab unit receives the suspect material wherein the suspect material may contain explosives resulting in the suspect material is being located on the lateral flow swab unit,
   a breakable ampoule positioned inside of bottle shaped container explosives tester body,
   an explosives detecting reagent contained in said breakable ampoule positioned inside of bottle shaped container explosives tester body,
   wherein said breakable ampoule containing said explosives detecting reagent is positioned inside of bottle shaped container explosives tester body and provides a dispenser that delivers said explosives detecting reagent to said lateral flow swab unit wherein said explosives detecting reagent and the suspect material that may contain explosives are located on the lateral flow swab unit, and
   a solvent front on said lateral flow swab unit,
   said solvent front created by said explosives detecting reagent and the suspect material that may contain explosives,
   said solvent front including the suspect material that may contain explosives, and
   said solvent front including said explosives detecting reagent, and
   said solvent front having the suspect material that may contain explosives concentrated in said solvent front.

2. The explosives tester apparatus for testing a suspect material for explosives of claim 1 wherein said lateral flow swab unit comprises a lateral flow membrane swab unit made of a microporous membrane that provides migration of said explosives detecting reagent from said dispenser and wherein the suspect material that may contain explosives is concentrated in said solvent front.

3. The explosives tester apparatus for testing a suspect material for explosives of claim 1 wherein said lateral flow swab unit comprises a lateral flow membrane swab unit made of polyethylene spheres fused into a lateral flow membrane that provides migration of said explosives detecting reagent from said dispenser and wherein the suspect material that may contain explosives is concentrated in said solvent front.

4. The explosives tester apparatus for testing a suspect material for explosives of claim 1 wherein said lateral flow swab unit comprises a lateral flow membrane swab unit made of a microporous cellulose membrane that provides migration of said explosives detecting reagent from said dispenser and wherein the suspect material that may contain explosives is concentrated in said solvent front.

5. The explosives tester apparatus for testing a suspect material for explosives of claim 1 wherein said lateral flow swab unit comprises a lateral flow membrane swab unit made of a microporous cellulose nitrate membrane that provides migration of said explosives detecting reagent from said dispenser and wherein the suspect material that may contain explosives is concentrated in said solvent front.

6. The explosives tester apparatus for testing a suspect material for explosives of claim 1 wherein said lateral flow swab unit comprises a plug made of a microporous membrane material that provides migration of said explosives detecting reagent from said dispenser and wherein the suspect material that may contain explosives is concentrated in said solvent front.

7. The explosives tester apparatus for testing a suspect material for explosives of claim 1 wherein said lateral flow swab unit comprises a cylindrical plug made of a microporous membrane material that provides migration of said explosives detecting reagent from said dispenser and wherein the suspect material that may contain explosives is concentrated in said solvent front.

8. The explosives tester apparatus for testing a suspect material for explosives of claim 1 wherein said bottle shaped container explosives tester body is a bottle shaped container made of a flexible plastic material and said breakable ampoule is inside of said bottle shaped container made of a flexible plastic material.

9. The explosives tester apparatus for testing a suspect material for explosives of claim 1 wherein said bottle shaped container explosives tester body is a bottle shaped container made of a flexible plastic material and wherein said container has an outlet with said lateral flow swab unit is positioned in said outlet of said container and wherein said breakable ampoule is inside said container made of a flexible plastic material.

10. The explosives tester apparatus for testing a suspect material for explosives of claim 1 wherein said explosives tester body is a container made of a flexible material and said dispenser is a breakable unit entirely inside of said container made of a flexible material.

11. The explosives tester apparatus for testing a suspect material for explosives of claim 1 wherein said explosives tester body is a container made of a flexible material and said dispenser is a breakable container unit entirely inside of said container made of a flexible material.

12. The explosives tester apparatus for testing a suspect material for explosives of claim 1 wherein said explosives tester body is a container made of a flexible material and said dispenser is a breakable glass ampoule inside of said body made of a flexible material.

13. The explosives tester apparatus for testing a suspect material for explosives of claim 1 wherein said explosives tester body is a container made of a flexible plastic material and said dispenser is a breakable glass ampoule inside of said body made of a flexible plastic material.

14. The explosives tester apparatus for testing a suspect material for explosives of claim 1 wherein said explosives tester body is a container made of a flexible plastic material and said dispenser comprises a breakable ampoule located entirely inside of said container.

15. The explosives tester apparatus for testing a suspect material for explosives of claim 1 wherein said explosives tester body is a container made of a flexible plastic material and said dispenser comprises a breakable glass ampoule located entirely inside of said container.

16. The explosives tester apparatus for testing a suspect material for explosives of claim 1 wherein said explosives tester body comprises a squeezable plastic body and said dispenser comprises a breakable ampoule located entirely inside of said squeezable plastic body.

17. The explosives tester apparatus for testing a suspect material for explosives of claim 1 wherein said explosives tester body comprises a squeezable plastic body and said dispenser comprises a breakable glass ampoule located entirely inside of said squeezable plastic body.

18. The explosives tester apparatus for testing a suspect material for explosives of claim 1 wherein said explosives tester body is a container made of a flexible material with an outlet and wherein said lateral flow swab unit is positioned in said outlet of said container and wherein said explosives detecting reagent comprises Meisenheimer complexes.

19. The explosives tester apparatus for testing a suspect material for explosives of claim 1 wherein said explosives tester body is a container made of a flexible material with an outlet and wherein said lateral flow swab unit is positioned in said outlet of said container and wherein said explosives detecting reagent comprises a Griess reagent.

20. The explosives tester apparatus for testing a suspect material for explosives of claim 1 wherein said explosives tester body is a container made of a flexible material with an outlet and wherein said lateral flow swab unit is positioned in said outlet of said container and wherein said explosives detecting reagent comprises a Nesslers reagent.

21. The explosives tester apparatus for testing a suspect material for explosives of claim 1 wherein said explosives tester body is a container made of a flexible material with an outlet and wherein said lateral flow swab unit is positioned in said outlet of said container and wherein said explosives detecting reagent comprises a thymol reagent.

22. The explosives tester apparatus for testing a suspect material for explosives of claim 1 wherein said explosives tester body is a container made of a flexible material with an outlet and wherein said lateral flow swab unit is positioned in said outlet of said container and wherein said explosives detecting reagent comprises diphenylamine/$H_2SO_4$.

23. The explosives tester apparatus for testing a suspect material for explosives of claim 1 wherein said explosives tester body is a container made of a flexible material with an outlet and wherein said lateral flow swab unit is positioned in said outlet of said container and wherein said explosives detecting reagent comprises tetra-n-butylammonium hydroxide or KOH in EtOH.

* * * * *